United States Patent
Mollica

(10) Patent No.: US 7,455,651 B2
(45) Date of Patent: Nov. 25, 2008

(54) ANTI-GRAVITY DECOMPRESSANT FOR LOWER EXTREMITIES

(76) Inventor: Natalia Mollica, 209 High Point Park, Frederica, DE (US) 19946

( * ) Notice: Subject to any disclaimer, the term of this patent is extended or adjusted under 35 U.S.C. 154(b) by 57 days.

(21) Appl. No.: 11/423,993

(22) Filed: Jun. 14, 2006

(65) Prior Publication Data

US 2007/0293802 A1    Dec. 20, 2007

(51) Int. Cl.
*A61F 13/00* (2006.01)
(52) U.S. Cl. .............. 602/65; 602/60; 602/62; 128/845; 128/846; 128/882
(58) Field of Classification Search ............ 5/630, 5/648, 651; 128/882, 846, 845; 602/23, 602/27, 28, 60–64, 65, 4, 5
See application file for complete search history.

(56) References Cited

U.S. PATENT DOCUMENTS

| | | | |
|---|---|---|---|
| 3,693,619 A | 9/1972 | Williams | |
| 4,186,738 A * | 2/1980 | Schleicher et al. | ........ 128/892 |
| 4,254,563 A | 3/1981 | Bruno | |
| 5,014,448 A | 5/1991 | Perrone | |
| 5,052,128 A | 10/1991 | Lonardo | |
| 5,226,245 A | 7/1993 | Lamont | |
| 5,449,339 A | 9/1995 | Drennan | |
| 5,609,570 A | 3/1997 | Lamont | |
| 5,797,862 A | 8/1998 | Lamont | |
| 5,827,211 A | 10/1998 | Sellinger | |
| 5,876,364 A | 3/1999 | Herbst | |
| 6,032,784 A | 3/2000 | Bellanca et al. | |
| 6,059,744 A | 5/2000 | Hardt | |
| 6,083,185 A | 7/2000 | Lamont | |
| 6,308,713 B1 | 10/2001 | Coleman et al. | |
| D453,969 S | 2/2002 | Callsen et al. | |
| 6,375,633 B1 | 4/2002 | Endress et al. | |
| 6,640,810 B1 | 11/2003 | Callsen et al. | |
| 7,022,096 B1 | 4/2006 | Alfieri et al. | |
| 2003/0217412 A1 * | 11/2003 | Johns et al. | ........... 5/636 |
| 2005/0251085 A1 * | 11/2005 | Fareed | ........... 602/65 |
| 2007/0100264 A1 * | 5/2007 | Hanson | ........... 602/2 |

* cited by examiner

*Primary Examiner*—Kim M Lewis
(74) *Attorney, Agent, or Firm*—Connolly Bove Lodge & Hutz LLP

(57) ABSTRACT

A textile anti-gravity decompressant for protecting a patient's heel and ankle includes a padded portion at an ankle region, and ventilation holes formed through the textile covering. The protector further has a strap closure with a fastener that mates with a fastener provided on the outer surface of the textile covering, and where the strap closure includes a patch or other covering over a portion of the fastener to prevent said strap closure from being secured too tightly over a person's heel or ankle.

10 Claims, 2 Drawing Sheets

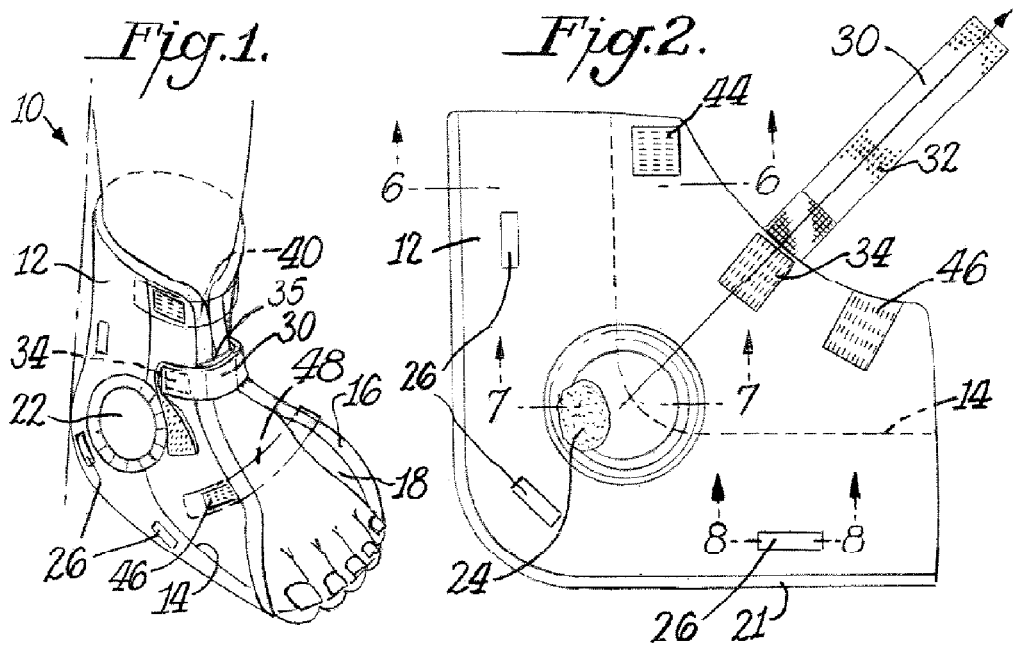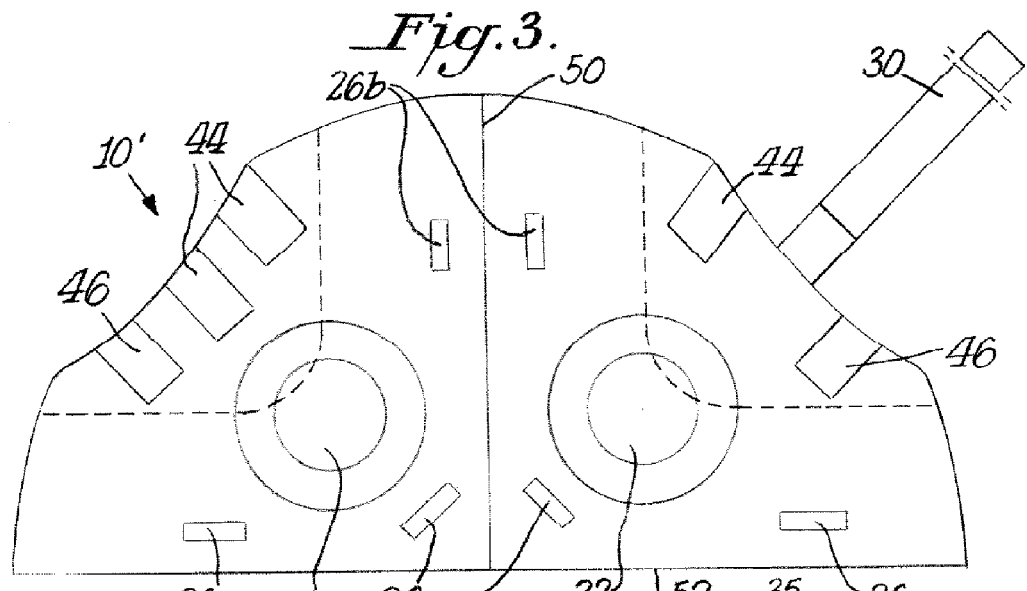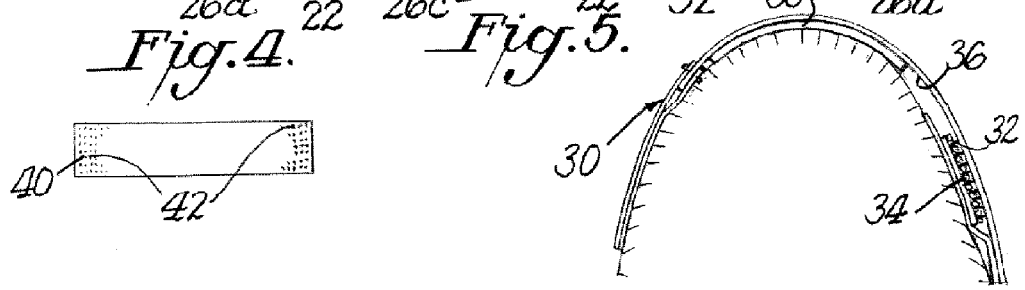

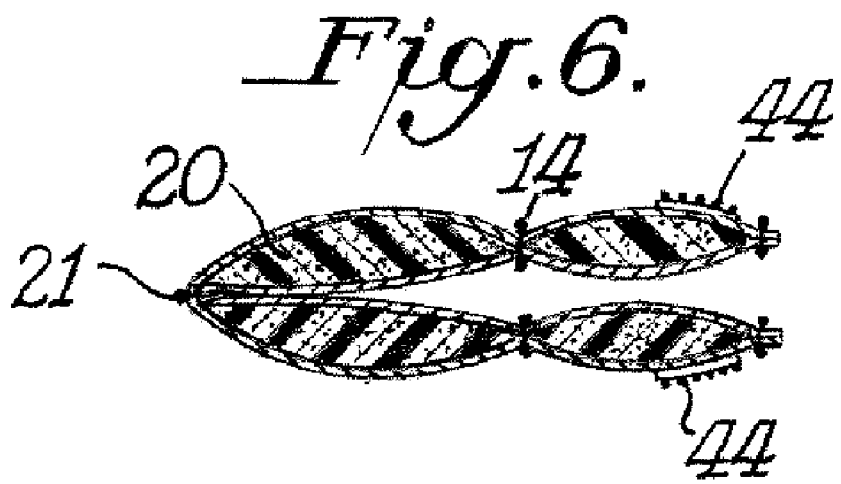
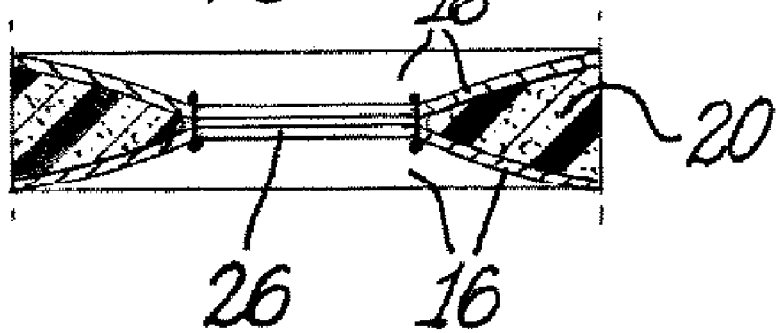

ANTI-GRAVITY DECOMPRESSANT FOR LOWER EXTREMITIES

BACKGROUND OF THE INVENTION

1. Field of the Invention

This invention relates to heel and ankle protector coverings or boots worn by hospital and nursing home patients to minimize pressure points on the heel and ankle and thus help such patients avoid developing bed sores or decubitis ulcers from prolonged contact with bedding or hard surfaces during a period of bedrest or inactivity.

2. Description of the Related Art

Various pads and cushions have been designed to protect the bony protuberances of a patient from prolonged contact with a bed surface when the patent is subjected to prolonged periods of bedrest to help avoid or minimize decubitis ulcers or bed sores from forming. Of particular concern are a patient's heel and ankle. Bedridden patients may experience ulcerative conditions (pressure sores or bed sores) on the skin and underlying tissues and bone of the ankles, feet, heels and toes.

Millions of people suffer from diabetes. Many diabetics further suffer from lower leg and specifically foot complications, such as diabetes mellitus, chronic thrombophlebitis, malnutrition and vitamin deficiency, carcinoma, multiple sclerosis, uremia, vascular disease, and venus statis ulcers. These conditions, if not treated, and if a patient's limb is not supported properly, can result in the loss of the patient's limb.

One foot protector design shown in U.S. Pat. No. 6,640,810 has a textile web or fabric boot-like structure that may be secured over a patient's foot with hook and loop fastener (Velcro) straps. Additional padding (such as foam) optionally is added to the protector to cover the ball and sides of the foot and the ankle bone. A single bottom opening in the protector exposes the patient's heel to air. No other ventilation means is provided. Nor are means provided to prevent over-tightening of the fastener straps. See also U.S. Pat. No. D453,969 S.

A heel protector shown in U.S. Pat. No. 6,308,713 has a cap formed of resiliently flexible material with a plurality of ventilation holes formed therein. The cap is held over a patient's heel with straps having hook and loop fasteners (Velcro). No extra padding is provided over the bony protuberances of the ankle. The resiliently flexible material appears to be a foam, rather than a textile or quilted textile. Thus, such material cannot be laundered, and will build up excessive heat in contact with the skin, which heat is not likely to be released satisfactorily by the ventilation holes.

A cushion protector shown in U.S. Pat. No. 3,693,619 comprises a convoluted foam piece that has been folded and stitched together at seam 13. A single ventilation hole at the heel region is provided. The protector is held over a patient's foot and secured with strings 21. No extra padding is provided over the bony protuberances of the ankle. The convoluted foam material cannot be laundered, and will build up excessive heat in contact with the skin. While the patent indicates that the convoluted foam surface provides increased ventilation, such foams have been demonstrated to build up heat, leading to patient discomfort. No means is provided to prevent over-tightening of the protector over the patient's foot.

U.S. Pat. No. 5,797,862 shows a medical boot for a patient with a diabetic foot. Such boot includes heat activated material at the insole to form a permanent impression of the bottom of a patient's foot. There is no provision for ventilation and no means is provided to prevent over-tightening of the boot over the patient's foot.

While heel and ankle boots or protectors are known generally, improvements in such foot/leg coverings are still sought. In these respects, the heel and ankle protector according to the present invention substantially departs from the conventional concepts and designs of the prior art, and in so doing provides a more comfortable foot covering for hospital and nursing home patients, and other incapacitated persons.

SUMMARY OF THE INVENTION

In a first embodiment, an anti-gravity decompressant boot or protector has a textile covering that may be quilted, and that has an inner surface adapted for contact with a person's heel and ankle and with an outer surface. The protector also has at least one padded portion at an ankle region of said textile covering to cushion the ankle bone. To increase air circulation to a patient's skin, a plurality of ventilation holes are formed through the textile covering.

The protector is held or secured over a patient's foot with at least one strap closure. The strap closure has a fastener that mates with a fastener provided on the outer surface of the textile covering. The strap closure includes means for preventing said strap closure from being secured too tightly over a person's heel or ankle. In the first embodiment, a portion of the strap closure lacks hook or loop fasteners (e.g., Velcro). In a second embodiment, a portion of the hook or loop fasteners on the strap closure are covered with a patch that prevents engagement with a mating hook or loop fastener on the outer surface of the protector.

A second strap closure and a third strap closure optionally may be used to further secure the protector around a patient's foot or ankle. In one embodiment, the second and third strap closures have hook or loop fasteners at their proximal and distal ends that mate with receiving hook or loop fasteners applied to the outer surface of the protector. A portion of the second and third strap closures may lack hook or loop fasteners (e.g., Velcro) or may be covered with a patch that prevents engagement with a mating hook or loop fastener on the outer surface of the protector.

BRIEF DESCRIPTION OF THE DRAWINGS

The invention will be better understood when consideration is given to the following detailed description. Such description makes reference to the annexed drawings wherein:

FIG. 1 is a perspective view of a protector according to the invention;

FIG. 2 is a left side elevational view of the protector shown in FIG. 1;

FIG. 3 is a pattern layout for the protector shown in FIGS. 1 and 2;

FIG. 4 is a top plan view of a second strap closure that optionally may be used with the protector according to the invention;

FIG. 5 is a top plan view of the strap closure for a protector that is attached around a patient's ankle;

FIG. 6 is a cross-sectional view taken along line 6-6 of FIG. 2 showing the quilted construction of the protector;

FIG. 7 is a cross-sectional view taken along line 7-7 of FIG. 2 showing the ankle protective pad; and FIG. 8 is an enlarged cross-sectional view taken along line 8-8 of FIG. 2 showing a ventilation hole through the protector.

DETAILED DESCRIPTION OF EMBODIMENTS OF THE INVENTION

With reference now to the drawings, and in particular to FIGS. 1-8, an anti-gravity decompressant or protector for protecting a patient's heel and ankle embodying the principles and concepts of the present invention and generally designated by the reference numeral 10 will be described.

The protector 10 comprises a quilted textile foot and ankle covering 12 having an outer fabric 16 and an inner fabric 18 with fiber fill, foam, memory foam or other quilt filling 20 therebetween. A preferred filling is memory foam (viscoelastic foam), which is known for its resilience and soft tactile property when subjected to compression. The inner fabric 18 and outer fabric 16 are held together by quilting stitching 14 such as shown in FIG. 1. Although one long quilting stitching 14 line is shown on each of the left and right sides of the protector 10, additional quilting with various stitching patterns are possible within the scope of this invention.

One possible pattern 10' for making a protector 10 is shown in FIG. 3. With such pattern 10', the elements of the protector 10 are placed generally symmetrically opposite a vertical center line 50. It is possible to secure or stitch together two mirror-image pieces (e.g. a right side and a left side), such as by stitching along center line 50 and bottom edge 52 to form the boot-like structure of the protector 10 shown in FIG. 1. Stitch line 21 in FIG. 2 joins two mirror-image pieces together. Alternatively, pieces may be joined by heat sealing, gluing or other joining technique.

The fabric forming the quilted textile foot covering 12 is selected for comfortable contact with a patient's foot and ankle. Preferably, such fabric is washable, such as with standard laundering and drying equipment found in residential homes, hospitals and nursing homes. Suitable fabrics include cotton, polyester cotton blends, wool cotton blends, spandex cotton blends, flannel and cotton fleece. The inner fabric 18 of the protector 10 is selected specifically so as to be soft and pleasing in contact with a patient's skin. Any fabrics that are known in the industry as hypo-allergenic are also suitable.

A protective ankle pad 22 is disposed on each of the right and left sides of the protector 10, generally symmetrically opposite vertical center back seam 50 (back seam 50 shown on pattern 10' in FIG. 3). The protective ankle pad 22 contains additional padding 24, such as memory foam (viscoelastic foam), to cushion the bony protuberance of the ankle bone. Ankle pads 22 are disposed on both sides of the protector 10 so that the protector 10 may be worn on either the right or left foot of the patient and still offer cushioning to the ankle bone. In this sense, the protector 10 is of a universal construction.

Preferably, ankle pad 22 has a generally circular or round periphery. While it is not required to be circular or round, a shape that adequately covers the bony ankle protuberance is desired. Preferably, the ankle pad 22 is a separable cushion structure that is applied to the outer fabric 16 by stitching, gluing, heat sealing or other attachment means. Alternatively, the ankle pad 22 may be integrally formed as a section of the quilting pattern within the protector between the inner fabric 18 and outer fabric 16. Foam or fiberfill padding within the ankle pad generally has a thickness of from 1 to 2 cm.

To improve air circulation to the patient's foot and ankle, ventilation holes 26 are formed through the protector 10. In one embodiment, the vent holes 26 are formed as elongated, button hole-like openings through the outer fabric 16, inner fabric 18 and quilting filling 20. While elongated openings are shown in the embodiment of FIGS. 1 and 2, other vent hole 26 configurations, such as regular or irregular shapes, are possible.

Referring to the pattern 10' (see FIG. 3) for making the protector 10, vent holes 26 are formed in pairs positioned at locations along the protector 10 symmetrically opposite vertical center line 50. The vent holes 26 may be oriented at angles variously to the vertical center line 50. As shown in FIG. 3, one pair of vent holes 26a are perpendicular to the vertical center line 50, another pair of vent holes 26b are parallel to the vertical center line 50, and a third pair of vent holes 26c are at an angle of about 45 degrees with respect to the vertical center line 50. Angles from 0 to 90 degrees with respect to the vertical center line 50 may be suitable. Three pairs of vent holes 26 are shown in the protector 10 of FIG. 1, and this is a preferred minimum configuration for vent holes in the protector 10. Of course, additional pairs of vent holes 26 may be provided as desired. Preferably, vent holes 26 are formed in pairs symmetrically opposite the vertical center line 50, but other arrangements of ventilation openings may be desired.

A first strap closure 30 is formed integrally in or attached to the right side of the protector 10. Preferably, the first strap closure 30 is joined to the protector 10, such as by stitching or gluing the proximal end of the strap closure 30 to the protector 10. The first strap closure 30 has a hook or loop fastener 32 (e.g., Velcro) at its distal end for attachment to a mating hook or loop fastener 34 (e.g., Velcro) provided on the outer fabric surface 16 of the left side of the protector 10. The first strap closure 30 additionally has a portion 36 of its surface at or near the proximal end of the first strap closure that is without hook or loop fastener 32 capable of attaching to mating hook or loop fastener 34. Such portion may be free of hook or loop fastener 32, or may be supplied with a patch 35 covering the hook or loop fastener 34. In this way, first strap closure 30 is prevented from being over-tightened over a patient's foot or ankle. The proximal portion of first strap closure 30 that lacks hook or loop fastener 32 or has a patch 35 covering the hook or loop fastener 32 cannot attach to hook or loop fastener 34 provided on the outer fabric surface 16 of protector 10.

We have found that prior heel and ankle protectors or boots have been secured too tightly over patients' feet and ankles, leading to reduced circulation to the feet. Health care workers tend to tie or secure hook and loop fasteners of prior art straps too tightly. The inventive heel and ankle protector thus has provided means to prevent over-tightening by covering the hook or loop fastener at or near the proximal end of the strap closure. FIG. 5 shows attachment of the protector over a patient's ankle, wherein the patch 35 prevents the first strap closure 30 from being joined to the mating fastener 34. Only fastener 32 attaches to mating fastener 34.

A second strap closure 40 optionally may be used to secure the protector 10 over a patient's ankle and foot. Such second strap closure 40 is provided with hook or loop fasteners 42 (e.g., Velcro) at its proximal and at its distal ends. Such hook or loop fasteners 42 mate with hook or loop fastener patches 44 on the outer fabric surface 16 of the left side and right side of the protector 10. The length of the second strap closure 40 may be varied to accommodate a patient's ankle size. Moreover, said second strap closure 40 is provided with a patch 35 to cover the fastener, or has a portion of such strap closure 40 without hook and loop fasteners, so that the second strap closure 40 is prevented from being over-tightened over a patient's foot or ankle.

A third strap closure 48 optionally may be used to secure the protector 10 over a patient's foot. Such third strap closure 48 is provided with hook or loop fasteners (e.g., Velcro) at its proximal and at its distal ends. Such hook or loop fasteners mate with hook or loop fastener patches 46 on the outer fabric surface 16 of the left side and right side of the protector 10.

The length of the third strap closure 48 may be varied to accommodate a patient's foot size. Moreover, said third strap closure 48 is provided with a patch 35 to cover the fastener, or has a portion of such strap closure 48 without hook and loop fasteners, so that the third strap closure 48 is prevented from being over-tightened over a patient's foot. The protector 10 is comfortably worn over a patient's foot and ankle when said patient is in bed, or is in a wheelchair or when a patient otherwise has limited mobility. The soft quilted fabric with memory foam filling particularly supports the patient's foot and ankle in comfort, helping to prevent formation of sores that otherwise might form due to contact with bedding or hard surfaces. The series of ventilation holes causes greater air circulation to the patient's skin. The protector 10 can be provided in various sizes, such as small, medium and large; it has a universal construction so that such protector 10 may be worn on the left foot or on the right foot.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Other embodiments of the invention will be apparent to those skilled in the art from a reading of the specification and practice of the invention disclosed herein. Therefore, the specification and examples are to be considered as exemplary, and the scope and spirit of the invention shall be indicated by the following claims.

What is claimed is:

1. A foot protector, comprising:
    a quilted textile covering with an inner fabric surface adapted for contact with a person's heel and ankle and with an outer surface;
    a padded portion at an ankle region of said textile covering;
    a plurality of ventilation holes formed through the textile covering;
    a strap closure for securing the textile covering over a person's heel and ankle, wherein said strap closure has a fastener that mates with a fastener provided on the outer surface of the textile covering, and wherein a patch covers a portion of the fastener at or proximate to the proximal end of the strap closure for preventing said strap closure from being secured too tightly over a person's heel or ankle.

2. The foot protector of claim 1, wherein the fastener on the strap closure is a hook portion of a hook and loop fastener and the fastener on the outer surface is a loop portion of a hook and loop fastener, and the patch is positioned over at least a portion of the hook portion at or near a proximal end of the strap closure.

3. The foot protector of claim 1, wherein the fastener on the strap closure is a loop portion of a hook and loop fastener and the fastener on the outer surface is a hook portion of a hook and loop fastener, and the patch is positioned over at least a portion of the loon portion at or near a proximal end of the strap closure.

4. The foot protector of claim 1, further comprising a second strap closure for securing the textile covering over a person's heel and ankle, wherein said second strap closure has a fastener at or near a distal end that mates with a receiving fastener provided on the outer surface of the textile covering.

5. The foot protector of claim 4, wherein the second strap closure further has a second fastener that mates with a second receiving fastener provided on the outer surface of the textile covering.

6. The foot protector of claim 1, wherein the ventilation holes are formed in pairs with each hole in a respective pair arranged symmetrically opposite a generally vertical back seam formed in the protector.

7. The foot protector of claim 1, wherein said textile covering is quilted by connecting a first fabric sheet forming the inner surface to a second fabric sheet forming the outer surface by stitching.

8. The foot protector of claim 7, wherein a fiber or foam quilting filling is disposed between the first and second fabrics.

9. The foot protector of claim 1, further comprising a second padded portion positioned opposite the padded portion such that the padded portion and the second padded portion are on opposite sides of a generally vertical back seam formed in the protector.

10. The foot protector of claim 1, wherein said protector may be laundered.

* * * * *